United States Patent [19]

Mori et al.

[11] 3,984,425

[45] Oct. 5, 1976

[54] PROCESS FOR PURIFYING 1-AMINOANTHRAQUINONE

[75] Inventors: Hidetoshi Mori; Ken Mukai; Koichi Yoshiura, all of Ohmuta, Japan

[73] Assignee: Mitsui Toatsu Chemicals, Incorporated, Tokyo, Japan

[22] Filed: Dec. 22, 1975

[21] Appl. No.: 642,799

[30] Foreign Application Priority Data

Feb. 13, 1975 Japan.............................. 50-17391

[52] U.S. Cl. .................................................. 260/378
[51] Int. Cl.² ........................................ C07C 97/24
[58] Field of Search ...................................... 260/378

[56] References Cited
UNITED STATES PATENTS 3,700,700   10/1972   Actermatt...................... 260/378 X
3,873,582   3/1975    Szekely............................... 260/378

Primary Examiner—Paul F. Shaver
Attorney, Agent, or Firm—Sherman & Shalloway

[57] ABSTRACT

A process for purifying 1-aminoanthraquinone, which comprises hydrogenating crude 1-aminoanthraquinone containing diaminoanthraquinones in an aqueous medium in the presence of a base using a hydrogenating catalyst to form a mixture comprising 1-aminoanthrahydroquinone and the corresponding diaminoanthrahydroquinones, partially oxidizing the mixture, removing water-insoluble materials from the oxidation product, and then oxidizing the remaining water-soluble residue.

6 Claims, No Drawings

PROCESS FOR PURIFYING 1-AMINOANTHRAQUINONE

This invention relates to a process for purifying 1-aminoanthraquinone.

1-Aminoanthraquinone can be obtained by reducing 1-nitroanthraquinone in a customary manner. Attempt to produce 1-nitroanthraquinone by nitration of anthraquinone, however, results in the formation of 2-nitroanthraquinone and various dinitro compounds in addition to the desired 1-nitroanthraquinone, and it is extremely difficult to recover 1-nitroanthraquinone in a pure form from the reaction mixture. Usually, the product obtained by the nitration of anthraquinone in sulfuric acid contains only 60 to 75% of 1-nitroanthraquinone. Reduction of this product does not afford the corresponding aminoanthraquinone that can be used as an intermediate for the synthesis of dyes. Accordingly, it is necessary to purify 1-nitroanthraquinone, and various methods have been suggested for this purpose, for example, treatment with a bisulfite, treatment with an organic solvent (e.g., dimethyl formamide), treatment with a base, or hydroxyamination. However, these purifying methods are difficult to afford 1-nitroanthraquinone having high purity, or can give pure 1-nitroanthraquinone in a low yield.

It is an object of this invention to provide a process for preparing 1-aminoanthraquinone of high purity from crude 1-aminoanthraquinone obtained by reducing crude 1-nitroanthraquinone or 1-nitroanthraquinone roughly purified in a known manner.

This object can be achieved in accordance with this invention by a process for purifying crude 1-aminoanthraquinone which comprises hydrogenating (reducing crude 1-aminoanthraquinone containing diaminoanthraquinones in an aqueous medium in the presence of a base using a hydrogenating catalyst to form a mixture comprising 1-aminoanthrahydroquinone and the corresponding diaminoanthrahydroquinones, partially oxidizing the mixture, removing water-insoluble materials from the oxidation product, and then oxidizing the remaining water-soluble residue.

The process of this invention is based on the utilization of the difference between the rate of oxidizing 1-aminoanthrahydroquinone to 1-aminoanthraquinone and the rate of oxidizing diaminoanthrahydroquinones to the corresponding diaminoanthraquinones. The diaminoanthrahydroquinones are oxidized at a faster rate than 1-aminoanthrahydroquinone. The rate of oxidizing 1,5-diaminoanthrahydroquinone is especially faster. Accordingly, substantially pure 1-aminoanthraquinone having an extremely low content of diaminoanthraquinones can be obtained by partially oxidizing the hydroquinone mixture in the presence of a base, separating water-soluble 1-aminoanthrahydroquinone remaining unoxidized in the product from water-insoluble diaminoanthraquinones (which is the oxidation reaction products) and the catalyst, and oxidizing the 1-aminoanthrahydroquinone.

In the partial oxidation of the mixture of 1-aminoanthrahydroquinone and diaminoanthrahydroquinones, air or other oxidizing agents can be used. The partial oxidation should be stopped at a time when the diaminoanthrahydroquinones have been oxidized substantially to diaminoanthraquinones. Then, the water-insoluble materials are removed, and the residue is again oxidized. This reaction proceeds easily.

The diaminoanthraquinones which can be removed by the process of this invention from crude 1-aminoanthraquinone are 1,5-, 1,8-, 1,6- and 1,7-diaminoanthraquinones.

Crude 1-aminoanthraquinone can be prepared by various methods. For example, it can be prepared by reducing crude 1-nitroanthraquinone in an aqueous alkali solution with a sulfur compound such as an alkali sulfide, an alkali hydrosulfide or an alkali polysulfide, a saccharide such as glucose, a hydrazine, or a dithionite, or in an acidic aqueous solution with sulfur dioxide or a metal such as iron, aluminum, zinc or copper, or by hydrogenating the crude 1-nitroanthraquinone in an organic solvent or an aqueous medium using a hydrogenation catalyst. It can also be obtained by treating crude 1-nitroanthraquinone with ammonia in a solvent to substitute an amino group for the nitro group. Another method involves reacting crude anthraquinone-1-sulfonic acid with ammonia at an elevated pressure. The crude 1-aminoanthraquinone can be used in the process of this invention either after isolation or without isolation.

The hydrogenation in this invention can be carried out by ordinary methods at atmospheric pressure or an elevated pressure. For example, according to the atmospheric pressure method, a reactor equipped with a stirrer and a hydrogen-introducing tube is charged with crude 1-aminoanthraquinone, an aqueous medium, an organic or inorganic base and a catalyst, and the reaction is carried out with stirring at a predetermined temperature while introducing hydrogen.

The base used in this invention may be inorganic or organic, and a mixture of two or more bases can also be used. Any bases can be used which can render 1-aminoanthrahydroquinone soluble in the aqueous medium, and are substantially inert. Examples of commercially advantageous bases include hydroxides, oxides, carbonates, acetates and phosphates of alkali metals or alkaline earth metals such as sodium, potassium, calcium, barium, or magnesium, ammonia, diethylamine, morpholine, piperidine, ethanolamine, piperazine, ethylenediamine, 1,4-diazabicyclooctane, and 1,7-diazaundecene. The amount of the base to be used is at least 1 mole, preferably 1 to 20 moles, per mole of the starting 1-aminoanthraquinone. Where the base is a hydroxide, it is used preferably in an amount of at least $2/n$ moles (n being the atomic valency of an alkali metal or alkaline earth metal) per mole of the starting 1-aminoanthraquinone.

The base can be added at any time before the partial oxidation reaction, but preferably, it is caused to be present in the reaction system before the initiation of the reducing reaction.

The aqueous medium used in this invention may be water alone, or may contain an organic solvent which can dissolve 1-aminohydroanthraquinone in the presence of bases and does not obstruct the hydrogenation reaction. Usually, however, the use of water alone suffices.

When water alone is used, its amount is 5 to 200 times, preferably 10 to 60 times, the weight of the starting material.

The organic solvent that can be used together with water should be inert to the reaction system, and its examples include aromatic hydrocarbons whose aromatic nucleus is substituted by one to several halogen atoms, aliphatic, araliphatic and cycloaliphatic hydrocarbons containing 5 to 12 carbon atoms, halogenated aliphatic hydrocarbons containing 1 to 6 carbon atoms and substituted by one to several halogen atoms, ethers such as anisole, dialkyl ethers, tetrahydrofuran or dioxane, aliphatic and cycloaliphatic ketones such as acetone, methyl ethyl ketone or cyclohexanone, and mono- or polyhydric aliphatic and cycloaliphatic alcohols containing 1 to 6 carbon atoms.

When the organic solvent is conjointly used, it may be added before or during the hydrogenation reaction. When the organic solvent is conjointly used, the post-treatment of the product (the removal of insoluble materials and the oxidation of soluble materials) subsequent to the hydrogenation reaction can be performed either after recovering the organic solvent or without recovering it.

The amount of the organic solvent that can be used is up to 50 times, preferably up to 20 times, the weight of the starting 1-aminoanthraquinone. The organic solvent is mixed with water in the above-mentioned amount to form the aqueous medium. The proportion of the organic solvent in the aqueous medium is generally not more than 40% by weight, preferably not more than 30% by weight.

The conjoint use of the organic solvent changes the properties of the interface between the reaction medium and the suspended materials, and brings about favorable results for the reaction. For example, the reaction can be carried out while maintaining the concentration of the slurry high, or the rate of reaction is somewhat increased. Even when the starting 1-aminoanthraquinone contains an organic solvent entrained from its manufacturing process, it is not necessary to remove it prior to use in the process of this invention.

In the process of this invention, a surface active agent that does not adversely affect the hydrogenation reaction can also be used. Examples of suitable surface active agents are nonionic surface active agents such as polyoxyethylene alkyl ethers or polyoxyethylene alkylaryl ethers, and anionic surface active agents such as alkylarylsulfonic acids. The amount of the surface active agent that can be used in this invention is 0.001 to 1.0 time, preferably 0.005 to 0.5 time, the weight of the starting 1-aminoanthraquinone.

The addition of a surface active agent changes the properties of the interface between the reaction medium and the suspended materials, and therefore, brings about favorable results for the reaction. For example, the reaction can be carried out while maintaining the concentration of the slurry high, and the reaction mixture can be stirred easily. Furthermore, the rate of reaction is somewhat increased. Generally, however, the reaction can be carried out satisfactorily even without using surface active agents.

The hydrogenating catalyst used in the process of this invention may be any hydrogenating catalyst usually employed for converting quinones to hydroquinones by catalytic hydrogenation. Examples include catalysts containing a metal such as palladium, platinum, ruthenium, rhodium, nickel, cobalt or copper as an active ingredient. Palladium catalysts supported on a carrier such as carbon, alumina, diatomaceous earth, or siliaa gel are especially suitable. The amount of the catalyst differs according to the reaction conditions and the type of the catalyst. But when the reaction is carried out using a supported palladium catalyst, the suitable amount of the catalyst is 0.01 to 1.0 part by weight, as palladium metal, per 100 parts by weight of the starting material. When the catalyst is used without a carrier, for example, in the case of palladium black, the suitable amount of the catalyst is 0.01 to 5.0 parts by weight per 100 parts by weight of the starting material.

The reaction temperature that can be used in this invention is 0° to 160°C., preferably 10° to 80°C., more preferably 15° to 60°C., and the reaction pressure is preferably from atmospheric pressure to 100 Kg/cm². The reaction in accordance with this invention, however, proceeds even at room temperature and at atmospheric pressure. When the reaction temperature is too high, undesirable by-products are liable to be formed.

When 1-aminoanthraquinone containing diamino isomers is hydrogenated by the above method, first the reduction of a monoamino isomer to its hydroquinone derivative takes place, and then the diamino isomers are reduced to their hydroquinone derivatives, whereupon the absorption of hydrogen stops. The resulting 1-aminoanthrahydroquinone and diamonanthrahydroquinones form soluble salts with bases, and dissolve in the aqueous medium.

After the stopping of hydrogen absorption, the resulting reaction mixture is reacted with an oxidizing agent to oxidize it partially. Examples of the oxidizing agent that can be used in this invention are air, oxygen, hydrogen peroxide, sodium peroxide, perborates, peroxides of organic acids or salts thereof, peroxides of organic acid anhydrides, persulfates, hypochlorites, bleaching powder, and chlorine. Of these, air is especially preferred. For example, by passing air into the filtrate at a temperature of 0° to 120°C., preferably 10° to 80°C., it can be oxidized. The time required for the oxidation is 0.5 to 10 hours, 0.5 to 5 hours under preferred conditions, and less than 0.5 hour under more preferred conditions.

The amount of the oxidizing agent is preferably in a slight excess of the equivalent weight of diaminoanthrahydroquinones in the filtrate (i.e., when oxygen is used, ½ mole per mole of the diaminoanthrahydroquinones). This amount can be easily determined from the analysis values of the diaminoanthraquinones in the starting crude 1-aminoanthraquinone.

As a result of the partial oxidation in the above-described manner, the diaminoanthrahydroquinones dissolved as soluble salts in the reaction mixture are oxidized to diaminoanthraquinones which separate as precipitates. On the other hand, a salt of 1-aminoanthrahydroquinone is present in the dissolved state without undergoing change. The reaction mixture is filtered to separate the diaminoanthraquinones and the catalyst. This filtration can be carried out usually in an atmosphere of air, but preferably in an atmosphere of an inert gas such as nitrogen. If desired, the catalyst can be separated by filtration after the end of the hydrogenation reaction and before the oxidation of diaminoanthrahydroquinones in the reaction mixture.

The filtrate left after the separation of the diaminoanthraquinones and the catalyst is oxidized with an oxidizing agent to convert 1-aminoanthrahydroquinone to 1-aminoanthraquinone. The type of the oxidizing agent and the oxidation conditions which can be used in this oxidation step are the same as those used in the oxidation of the diaminoanthrahydroquinones. The preferred amount of the oxidizing agent is one which is in a slight excess of the equivalent weight to the 1-aminoanthrahydroquinone in the filtrate.

The end point of the oxidation reaction can be detected from the absence of a yellow oozed portion ascribable to 1-aminoanthrahydroquinone when the filtrate is dropped onto a filter paper. The resulting 1-aminoanthraquinone precipitates as crystals. The reaction mixture is filtered to afford 1-aminoanthraquinone of high purify free from the diaminoanthraquinones.

Generally, the process of this invention can be applied to the purification of crude 1-aminoanthraquinone having a diaminoanthraquinone content of not more than 50% by weight, especially not more than 25% by weight.

According to the process of this invention, high purity 1-aminoanthraquinone having a purity of at least 97% by weight with a diamino isomer content of less than 2% by weight, and under preferred conditions, having a purity of at least 99% by weight with a diamino isomer content of less than 1% by weight, can be obtained.

The crude 1-aminoanthraquinone used in this invention may contain anthraquinone or 2-aminoanthraquinone in addition to the diaminoanthraquinones. When such a starting material is used, another suitable purifying method may be employed before or after the process of this invention is performed.

The process of this invention can afford 1-aminoanthraquinone of good quality in good yields, and the product is very valuable as a dye intermediate. In addition, since the present invention permits a very simple purification of 1-aminoanthraquinone, it can be performed easily on a commercial basis.

The following Examples specifically illustrate the present invention.

EXAMPLE 1

A 1-liter electromagnetically stirred cylindrical glass reactor was charged with 5.0 g of crude 1-aminoanthraquinone having a purity of 92% and containing 5% of 1,5-diaminoanthraquinone and 2% of 1,8-diaminoanthraquinone (0.0206 mole of 1-aminoanthraquinone), 100 g (0.1 mole as sodium hydroxide) of a 4% aqueous solution of sodium hydroxide, and 0.15 g of 5% palladium-carbon. The inside of the reactor was purged with hydrogen, and the crude 1-aminoanthraquinone was hydrogenated with stirring at 30°C. In 5 hours when 0.022 mole of hydrogen was absorbed, the reaction stopped. The hydrogen in the reactor was replaced by nitrogen, and air was passed at 20° to 30°C. for 2 hours. The introduction of air was stopped when the amount of air absorbed reached 0.001 mole, calculated as oxygen. The resulting precipitate was separated by filtration together with the catalyst. The filtrate was oxidized with air. The crystals precipitated were filtered, washed with water, and dried to afford 4.4 g of 1-aminoanthraquinone. The product was found to have a purity of 99% by an infrared absorption spectroscopic method, and to contain a trace of 1,8-diaminoanthraquinone by a thin-layer chromatographic analysis. The yield of the product on a purity basis (the yield based on the pure 1-aminoanthraquinone content of the starting material) was 94.7%.

When the above procedure was repeated except that an aqueous solution containing 0.1 mole of potassium hydroxide, 0.052 mole of calcium hydroxide, or 0.048 mole of barium hydroxide was used instead of the aqueous solution of sodium hydroxide, the same results were obtained.

EXAMPLE 2

A 500 ml. electromagnetically stirred autoclave was charged with 5.0 g of crude 1-aminoanthraquinone having a purity of 92% and containing 5% of 1,5-diaminoanthraquinone and 2% of 1,8-diaminoanthraquinone, 100 g of a 4% aqueous solution of sodium hydroxide and 0.5 g of Raney nickel. The crude 1-aminoanthraquinone was hydrogenated with stirring at room temperature and 3 to 5Kg/cm$^2$.G. In 5 hours when the amount of hydrogen absorbed reached 0.022 mole, the reaction was stopped. The catalyst was removed from the reaction mixture. The filtrate was transferred to a 500 cc glass reactor, and nitrogen was introduced into the reactor. Then, at 30°C. air (0.001 mole calculated as oxygen) was caused to be absorbed by the filtrate over the course of 2 hours. The precipitate obtained was filtered. The filtrate was oxidized with air to afford 4.5 g of 1-aminoanthraquinone. The product was found to have a purity of 99% by an infrared absorption spectrocoscopic method, and its thin-layer chromatographic analysis did not detect 1,5-diaminoanthraquinone but showed the presence of traces of 1,8-diaminoanthraquinone and other diaminoanthraquinones. The yield of the product was 97% on a purity basis.

When the above procedure was repeated except that 30% hydrogen peroxide, a 15% aqueous solution of sodium hypochlorite or sodium perborate was used instead of the air in the oxidation treatment, the same results were obtained.

EXAMPLE 3

A 500 ml. electromagnetically stirred autoclave was charged with 5.0 g (0.0178 mole of 1-nitroanthraquinone) of 1-nitroanthraquinone (having a purity of 90% and containing 5% of 1,5-dinitroanthraquinone, 3% of 1,8-dinitroanthraquinone and 2% of 1,6- and 1,7-dinitroanthraquinones) prepared by nitrating anthraquinone with nitric acid in sulfuric acid and roughly purifying the product, 100 g of a 4% aqueous solution of sodium hydroxide (0.1 mole as sodium hydroxide) and 0.15 g of 5% palladium-carbon. The inside of the autoclave was purged with hydrogen, and the 1-nitroanthraquinone was hydrogenated with stirring at 30°C. In about 4 hours, the reaction stopped with the absorption of 0.083 mole of hydrogen. The hydrogen in the autoclave was replaced by nitrogen, and 0.00126 mole, calculated as oxygen, of air was caused to be absorbed by the reaction mixture at 30°C. over the course of 2 hours. The resulting precipitate was separated by filtration together with the catalyst. The filtrate was oxidized with air. The crystals precipitated were filtered, washed with water, and dried to afford 3.81 g of 1-aminoanthraquinone. As a result of a thin-layer chromatographic analysis, this product was found to be free from 1,5- and 1,8-diaminoanthraquinones and contain only traces of other diaminoanthraquinones. The purity of the product was more than 99% when determined by infrared absorption spectroscopy. The yield of the product was 95% on a purity basis.

What we claim is:

1. A process for purifying 1-aminoanthraquinone, which comprises hydrogenating crude 1-aminoanthraquinone containing diaminoanthraquinones in an aqueous medium in the presence of a base using a hydrogenating catalyst to form a mixture comprising 1-aminoanthrahydroquinone and the corresponding diaminoanthrahydroquinones, partially oxidizing the mixture, removing water-insolube materials from the oxidation product, and then oxidizing the remaining water-soluble residue.

2. The process of claim 1 wherein the aqueous medium is water.

3. The process of claim 1 wherein the aqueous medium is a mixture of water and an organic solvent, the proportion of the latter being not more than 40% by weight.

4. The process of claim 3 wherein the organic solvent is selected from the group consisting of aromatic hydrocarbons optionally substituted by one to several halogen atoms, aliphatic, araliphatic and cycloaliphatic hydrocarbons containing 5 to 12 carbon atoms, halogenated aliphatic hydrocarbons substituted by one to several halogen atoms and containing 1 to 6 carbon atoms, ethers selected from the group consisting of anisole, dialkylethers, tetrahydrofuran and dioxane, aliphatic and cycloaliphatic ketones, and monohydric and polyhydric aliphatic and cycloaliphatic alcohols containing 1 to 6 carbon atoms.

5. The process of claim 1 wherein an alkali metal or alkaline earth metal hydroxide is added as the base in an amount of at least $2/n$ moles per mole of the 1-aminoanthraquinone, in which $n$ represents the atomic valency of the alkali metal or alkaline earth metal, at the outset of, or during, the hydrogenation.

6. The process of claim 4 wherein the organic solvent is selected from the group consisting of acetone, methyl ethyl ketone and cyclohexanone.

* * * * *